United States Patent
Crosby et al.

(10) Patent No.: US 6,455,469 B1
(45) Date of Patent: Sep. 24, 2002

(54) HERBICIDAL COMPOSITION

(75) Inventors: Kevin E. Crosby, Concord; Jeffrey R. Schussler, Chardon, both of OH (US); Takahiro Haga, Shiga-ken (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 09/729,233

(22) Filed: Dec. 5, 2000

(51) Int. Cl.$^7$ .................. A01N 37/34; A01N 33/08; A01N 33/10; A01N 57/02; A01N 43/54
(52) U.S. Cl. .................. 504/127; 504/130; 504/131; 504/133; 504/136; 504/137; 504/138; 504/139; 504/140; 504/141; 504/142; 504/143; 504/144; 504/146; 504/147; 504/148
(58) Field of Search .................. 507/136, 127, 507/130, 131, 133, 137, 138, 139, 140, 141, 142, 143, 144, 146, 147, 148

(56) References Cited

U.S. PATENT DOCUMENTS

| | | | |
|---|---|---|---|
| 3,535,377 A | 10/1970 | Steinbrunn et al. | 260/562 |
| 3,965,139 A | 6/1976 | Scozzie | 71/105 |
| 4,001,325 A | 1/1977 | Bluestone et al. | 71/118 |
| 4,146,387 A | 3/1979 | Thiele | 71/118 |
| 4,277,278 A | 7/1981 | Eicken et al. | 71/118 |
| 5,741,756 A | 4/1998 | Shribbs | 504/149 |
| 6,001,774 A | 12/1999 | Mito | 504/130 |
| 6,121,201 A1 * | 9/2001 | Pulman et al. | 504/230 |

FOREIGN PATENT DOCUMENTS

| | | |
|---|---|---|
| DE | 19919951 | 9/1999 |
| WO | WO 97/34484 | 9/1997 |

OTHER PUBLICATIONS

Abstract JP 59093003 May 29, 1884.
Abstract JP 5908960 May 23, 1984.
Abstract JP 55049302 Apr. 9, 1980.
Abstract JP 54026823 Mar. 3, 1979.
Abstract JP 48008938.
Abstract JP 10231220 Sep. 2, 1998.
Abstract JP 09255511 Sep. 30, 1997.
Abstract JP 07048209 Feb. 21, 1995.
Abstract JP 06072809 Mar. 15, 1994.
Abstract JP 05255010 Oct. 5, 1993.
Abstract JP 01261311 Oct. 18, 1989.
Abstract JP 10231212 Sep. 2, 1998.
Abstract EP 714602 Jun. 5, 1996.
Abstract CN 1144601 Mar. 12, 1997.
Abstract DE 19859224 May 6, 1999.

* cited by examiner

Primary Examiner—S. Mark Clardy
(74) Attorney, Agent, or Firm—Sughrue Mion, PLLC

(57) ABSTRACT

The present invention provides to a herbicidal composition comprising as the effective components A) at least one substituted acetanilide derivative of the formula I:

☐EMBED ChemDraw.Document.4.5 ☐☐☐ wherein n is an integer of 1 or 2
R is H, halogen, C1–4 alkyl or C1–2 alkoxy
Q is cyanomethyl or propargyl
X is halogen B) at least one compound selected from the group consisting of aryloxyalkanoic acids, aromatic carboxylic acids, ureas, triazines, anilides, hydroxybenzonitriles, quaternary ammonium salts, triketones, aryloxyphenoxypropionic acids, oximes, sulfonylureas, imidazolinones, dinitroanilines, chloroacetanilides, oxyacetamides, thiocarbamates, amides, semicarbazones, amino acids, and inhibitors of protoporphyrinogen oxidase that includes diphenyl ethers, substituted uracils, pyrazoles, triazolinones and triazolopyridinones.

8 Claims, No Drawings

HERBICIDAL COMPOSITION

The present invention relates to a herbicidal composition comprising as the effective components at least one substituted acetanilide and at least one other specific herbicidal compound.

BACKGROUND OF THE INVENTION

U.S. Pat. No. 3,965,139 and U.S. Pat. No. 4,001,325 disclose certain substituted acetanilide derivatives as active ingredients for herbicides. The compounds disclosed in these patents are useful as herbicides for controlling grass weeds and certain broadleaf weeds. However, many weeds are not controlled by these herbicides, thus limiting their use for practical weed control in important crops. It has been found that mixing the acetanilide compounds of the above patents with other herbicides produces practical combinations which give effective weed control. Furthermore, unexpected differences in crop safety were found in certain combinations, resulting in unpredicted, preferred combinations and less preferred combinations with reduced crop safety.

SUMMARY OF THE INVENTION

The present invention provides to a herbicidal composition comprising as the effective components
A) at least one substituted acetanilide derivative of the formula I:

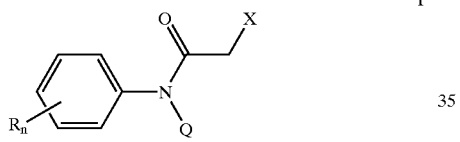

wherein n is an integer of 1 or 2
R is H, halogen, $C_{1-4}$ alkyl or $C_{1-2}$ alkoxy
Q is cyanomethyl or propargyl
X is halogen; and
B) at least one compound selected from the group consisting of aryloxyalkanoic acids, aromatic carboxylic acids, ureas, triazines, anilides, hydroxybenzonitriles, quaternary ammonium salts, triketones, aryloxyphenoxypropionic acids, oximes, sulfonylureas, imidazolinones, dinitroanilines, chloroacetanilides, oxyacetamides, thiocarbamates, amides, semicarbazones and inhibitors of protoporphyrinogen oxidase that include diphenyl ethers, substituted uracils, N-phenylphthalimides, pyrazoles, triazolinones and triazolopyridinones.

DETAILED DESCRIPTION OF THE INVENTION

In the above definitions, the term halogen includes fluorine, chlorine, bromine, or iodine. The term alkyl includes straight chain or branched alkyls containing 1–4 carbon atoms.

Compositions of the present invention are as follows.
The effective components are
A) at least one substituted chloroacetanilide derivative of the formula I;
 wherein n is an integer of 1 or 2
 R is H, halogen, $C_{1-4}$ alkyl or $C_{1-2}$ alkoxy
 Q is cyanomethyl (—$CH_2CN$) or propargyl (—$CH_2$—C≡CH)
 X is halogen; and
B) at least one compound selected from the group consisting of aryloxyalkanoic acids such as 2,4-D, 2,4-DB, MCPA or MCPB; aromatic carboxylic acids such as 2,3,6-TBA, Dicamba Picloram or Clopyralid; ureas such as Diuron, Linuron, Isoproturon, Chlorotoluron, Metobenzuron, Tebuthiuron or Fluometuron; triazines such as Simazine, Atrazine, Cyanazine, Terbuthylazine, Atraton, Hexazinone, Metribuzin, Simetryn, Ametryn, Prometryn, Dimethametryn or Triaziflam; anilides such as Propanil or Cypromid; hydroxybenzonitriles such as Bromoxynil-octanoate, Bromoxynil or Ioxynil; quaternary ammonium salts such as Paraquat, Paraquat-dichlorid, Diquat or Difenzoquat; diphenyl ethers such as Lactofen, Acifluorfen, Acifluorfen-sodium, Oxyfluorfen, Fomesafen, Bifenox or Chlomethoxyfen; triketones such as Sulcotrione or Mesotrione; aryloxyphenoxypropionic acids such as Diclofop-methyl, Pyrofenop-sodium, Fluazifop-butyl, Fluazifop-p-butyl, Haloxyfop-methyl, Quizalofop-p-ethyl, Quizalofop-p-tefuryl, Fenoxaprop-ethyl, Fenoxaprop-p-ethyl, Cyhalofopbutyl or Clodinafpop-p-propargyl; oximes such as Alloxydim-sodium, Sethoxydim, Clethodim, Tepraloxydim, Tralkoxydim or Cycloxydim; sulfonylureas such as Chlorimuron-ethyl, Nicosulfuron, Metsulfuron-methyl, Triasulfuron, Primisulfuron-methyl, Tribenuron-methyl, Chlorosulfuron, Bensulfuron-methyl, Sulfometuron-methyl, Prosulfuron, Halosulfuron, Halosulfuron-methyl, Thifensulfuron-methyl, Rimsulfuron, Azimsulfuron, Flazasulfuron, Imazosulfuron, Cyclosulfamuron, Flupyrsulfuron, Iodosulfuron, Ethoxysulfuron, Flucarbazone, Sulfosulfuron, Oxasulfuron or Foramsulfuron; imidazolinones such as Imazapyr, Imazethapyr, Imazaquin, Imazamox, Imazameth, Imazamethabenz-methyl or Imazapic; dinitroanilines such as Trifluralin, Oryzalin, Pendimethalin, Ethalfluralin, Benfluralin or Prodiamine; chloroacetanilides such as Alachlor, Metolachor, Metolachor-S, Propachlor, Acetochlor, Acetochlor-S, Propisochlor or Dimethenamid; oxyacetamides such as Flufenacet; thiocarbamates such as Thiobencarb, EPTC, Triallate, Molinate, Pebulate, Cycloate, Butylate, Vernolate or Prosulfocarb; amides such as Diphenamid; semicarbazones such as Diflufenzopyr; triazolinones such as Carfentrazone, Sulfentrazone or Amicarbazone; N-phenylphthalimides such as Flumioxazin; substituted uracils such as Benzfendizone, Butafenacil, 1-Amino-3-(4-chloro-2-fluoro-5-phenoxyphenyl)-6-(trifluoromethyl)-2,4(1H,3H)-pyrimidinedione, N-[3-Chloro-6-(3,6-dihydro-3-methyl-2,6-dioxo-4-(trifluoromethyl)-1(2H)-pyrimidinyl)-5-fluoro-2-methoxyphenyl]-2-naphthalenecarboxamide, [3-Chloro-6-(3,6-dihydro-3-methyl-2,6-dioxo-4-(trifluoromethyl)-1(2H)-pyrimidinyl)-5-fluoro-2-methoxyphenyl]-carbamic acid (3-nitrophenyl)methyl ester or 1-Amino-3-[4-chloro-2-fluoro-5-(2-nitrophenoxy)phenyl]-6-(trifluoromethyl)-2,4(1H,3H)-pyrimidinedione; isoxazolidinones such as Clomazone; quinoline carboxylic acids such as Quinclorac; isoxazoles such as Isoxaflutole or Isoxachlortole; amino acids such as Glyphosate or Glufosinate; and triazolopyridinones such as Azafenidine.

Preferred compositions of the present invention are as follows.

(1) The effective component
A) is at least one substituted acetanilide of the formula I;
   wherein n is an integer of 1 or 2
   R is H, halogen, $C_{1-4}$ alkyl or $C_{1-2}$ alkoxy
   Q is cyanomethyl or propargyl
   X is chlorine.

(2) The effective component B) is at least one compound selected from the group consisting of triazines such as Simazine, Atrazine, Cyanazine, Terbuthylazine, Atraton, Hexazinone, Metribuzin, Simetryn, Ametryn, Prometryn, Dimethametryn or Triaziflam; diphenyl ethers such as Lactofen, Acifluorfen, Acifluorfen-sodium, Oxyfluorfen, Fomesafen, Bifenox or Chlomethoxyfen; chloroacetanilides such as Alachlor, Metolachor, Metolachor-S, Propachlor, Acetochlor, Acetochlor-S, Propisochlor or Dimethenamid; triazolinones such as Carfentrazone, Sulfentrazone or Amicarbazone; N-phenylphthalimides such as Flumioxazin; substituted uracils such as Benzfendizone, Butafenacil, 1-Amino-3-(4-chloro-2-fluoro-5-phenoxyphenyl)-6-(trifluoromethyl)-2,4(1H,3H)-pyrimidinedione, N-[3-Chloro-6-(3,6-dihydro-3-methyl-2,6-dioxo-4-(trifluoromethyl)-1(2H)-pyrimidinyl)-5-fluoro-2-methoxyphenyl]-2-naphthalenecarboxamide, [3-Chloro-6-(3,6-dihydro-3-methyl-2,6-dioxo-4-(trifluoromethyl)-1(2H)-pyrimidinyl)-5-fluoro-2-methoxyphenyl]-carbamic acid (3-nitrophenyl)methyl ester or 1-Amino-3-[4-chloro-2-fluoro-5-(2-nitrophenoxy)phenyl]-6-(trifluoromethyl)-2,4(1H,3H)-pyrimidinedione; isoxazoles such as Isoxaflutole or Isoxachlortole; and triazolopyridinones such as Azafenidin.

More preferred compositions of the present invention are as follows.

(1) The effective components are
A) at least one substituted acetanilide derivative of the formula I;
   wherein n is an integer of 1 or 2;
   R is H, halogen, $C_{1-4}$ alkyl or $C_{1-2}$ alkoxy;
   Q is cyanomethyl or propargyl;
   X is chlorine; and
B) at least one compound selected from the group consisting of triazines such as Simazine, Atrazine, Cyanazine, Terbuthylazine, Atraton, Hexazinone, Metribuzin, Simetryn, Ametryn, Prometryn, Dimethametryn or Triaziflam; diphenyl ethers such as Lactofen, Acifluorfen, Acifluorfen-sodium, Oxyfluorfen, Fomesafen, Bifenox or Chlomethoxyfen; chloroacetanilides such as Alachlor, Metolachor, Metolachor-S, Propachlor, Acetochlor, Acetochlor-S, Propisochlor or Dimethenamid; triazolinones such as Carfentrazone, Sulfentrazone or Amicarbazone; N-phenylphthalimides such as Flumioxazin; substituted uracils such as Benzfendizone, Butafenacil, 1-Amino-3-(4-chloro-2-fluoro-5-phenoxyphenyl)-6-(trifluoromethyl)-2,4(1H,3H)-pyrimidinedione, N-[3-Chloro-6-(3,6-dihydro-3-methyl-2,6-dioxo-4-(trifluoromethyl)-1(2H)-pyrimidinyl)-5-fluoro-2-methoxyphenyl]-2-naphthalenecarboxamide, [3-Chloro-6-(3,6-dihydro-3-methyl-2,6-dioxo-4-(trifluoromethyl)-1(2H)-pyrimidinyl)-5-fluoro-2-methoxyphenyl]-carbamic acid (3-nitrophenyl)methyl ester or 1-Amino-3-[4-chloro-2-fluoro-5-(2-nitrophenoxy)phenyl]-6-(trifluoromethyl)-2,4(1H,3H)-pyrimidinedione; isoxazoles such as Isoxaflutole or Isoxachlortole; and triazolopyridinones such as Azafenidin.

(2) The effective component
A) is at least one substituted acetanilide derivative of the formula I;
   wherein n is an integer of 1 or 2
   R is $C_{1-4}$ alkyl
   Q is cyanomethyl or propargyl
   X is chlorine.

(3) The effective component B) is at least one compound selected from the group consisting of triazines such as Simazine, Atrazine, Cyanazine, Terbuthylazine, Atraton, Hexazinone, Metribuzin, Simetryn, Ametryn, Prometryn, Dimethametryn or Triaziflam; chloroacetanilides such as Alachlor, Metolachor, Metolachor-S, Propachlor, Acetochlor, Acetochlor-S, Propisochlor or Dimethenamid; substituted uracils such as Benzfendizone, Butafenacil, 1-Amino-3-(4-chloro-2-fluoro-5-phenoxyphenyl)-6-(trifluoromethyl)-2,4(1H,3H)-pyrimidinedione, N-[3-Chloro-6-(3,6-dihydro-3-methyl-2,6-dioxo-4-(trifluoromethyl)-1(2H)-pyrimidinyl)-5-fluoro-2-methoxyphenyl]-2-naphthalenecarboxamide, [3-Chloro-6-(3,6-dihydro-3-methyl-2,6-dioxo-4-(trifluoromethyl)-1(2H)-pyrimidinyl)-5-fluoro-2-methoxyphenyl]-carbamic acid (3-nitrophenyl)methyl ester or 1-Amino-3-[4-chloro-2-fluoro-5-(2-nitrophenoxy)phenyl]-6-(trifluoromethyl)-2,4(1H,3H)-pyrimidinedione; and isoxazoles such as Isoxaflutole or Isoxachlortole.

Most preferred compositions of the present invention are as follows.

(1) The effective component
A) is at least one substituted acetanilide derivative of the formula I;
   wherein n is an integer of 2
   R is methyl or ethyl
   Q is cyanomethyl or propargyl
   X is chlorine.

(2) The effective component B) is at least one compound selected from the group consisting of Simazine, Atrazine, Cyanazine, Terbuthylazine, Atraton, Hexazinone, Metribuzin, Simetryn, Ametryn, Prometryn, Dimethametryn and Triaziflam.

(3) The effective component B) is at least one compound selected from the group consisting of Alachlor, Metolachor, Metolachor-S, Propachlor, Acetochlor, Acetochlor-S, Propisochlor and Dimethenamid.

(4) The effective component B) is at least one compound selected from the group consisting of Benzfendizone, Butafenacil, 1-Amino-3-(4-chloro-2-fluoro-5-phenoxyphenyl)-6-(trifluoromethyl)-2,4(1H,3H)-pyrimidinedione, N-[3-Chloro-6-(3,6-dihydro-3-methyl-2,6-dioxo-4-(trifluoromethyl)-1(2H)-pyrimidinyl)-5-fluoro-2-methoxyphenyl]-2-naphthalenecarboxamide, [3-Chloro-6-(3,6-dihydro-3-methyl-2,6-dioxo-4-(trifluoromethyl)-1(2H)-pyrimidinyl)-5-fluoro-2-methoxyphenyl]-carbamic acid (3-nitrophenyl)methyl ester and 1-Amino-3-[4-chloro-2-fluoro-5-(2-nitrophenoxy)phenyl]-6-(trifluoromethyl)-2,4(1H,3H)-pyrimidinedione.

(5) The effective component B) is at least one compound selected from the group consisting of Isoxaflutole and Isoxachlortole.

The substituted acetanilide derivatives of the formula I include those shown in the following Table 1.

TABLE 1

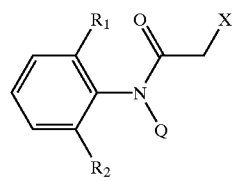

The substituted acetanilide derivatives

| No | X | R1 | R2 | Q |
|----|---|------|------|------|
| 1 | Cl | ethyl | ethyl | Cyanomethyl |
| 2 | Cl | methyl | H | Cyanomethyl |
| 3 | Br | ethyl | H | Cyanomethyl |
| 4 | Cl | ethyl | methyl | Cyanomethyl |
| 5 | Cl | methyl | methyl | Cyanomethyl |
| 6 | Cl | Cl | methyl | Cyanomethyl |
| 7 | F | F | H | Cyanomethyl |
| 8 | Cl | methyl | Isopropyl | Cyanomethyl |
| 9 | Cl | methoxy | H | Cyanomethyl |
| 10 | Cl | Cl | H | Cyanomethyl |
| 11 | Cl | isopropyl | H | Cyanomethyl |
| 12 | Cl | isopropyl | Isopropyl | Cyanomethyl |
| 13 | Cl | Br | H | Cyanomethyl |
| 14 | F | ethoxy | methoxy | Cyanomethyl |
| 15 | Cl | methyl | ethyl | Propargyl |
| 16 | Cl | ethyl | ethyl | Propargyl |
| 17 | Cl | methyl | H | Propargyl |
| 18 | Cl | ethyl | H | Propargyl |

TABLE 1-continued

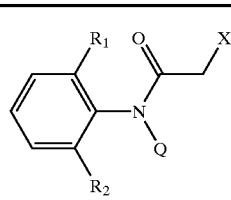

The substituted acetanilide derivatives

| No | X | R1 | R2 | Q |
|----|---|------|------|------|
| 19 | Cl | isopropyl | isopropyl | Propargyl |
| 20 | Cl | methyl | isopropyl | Propargyl |
| 21 | Cl | ethyl | isopropyl | Propargyl |
| 22 | Cl | isopropyl | H | Propargyl |
| 23 | Cl | methyl | methyl | Propargyl |

The compounds in Table 1 can be synthesized by the method disclosed in patents U.S. Pat. No. 3,965,139 and U.S. Pat. No. 4,001,325.

Other specific herbicidal compounds useful in combinations include those shown in the following Table 2.

TABLE 2

Herbicides useful for combinations with compounds of table 1. (Note: When a common name has not been assigned a compound, only the chemical name is provided)

Aryloxyalkanoic acids

| | | |
|---|---|---|
| B-1; | 2,4-D | (2,4-dichlorophenoxy)acetic acid |
| B-2; | 2,4 DB | 4-(2,4-dichlorophenoxy)butyric acid |
| B-3; | MCPA | 4-chloro-o-tolyloxyacetic acid |
| B-4; | MCPB | 4-(4-chloro-o-tolyloxy)butyric acid |

Aromatic carboxylic acids

| | | |
|---|---|---|
| B-5; | 2,3,6-TBA | 2,3,6 trichlorobenzoic acid |
| B-6; | Dicamba | 3,6-dichloro-o-anisic acid |
| B-7; | Picloram | 4-amino-3,5,6-trichloropyridine-2-carboxylic acid |
| B-8; | Clopyralid | 3,6-dichloropyridine-2-carboxylic acid |

Ureas

| | | |
|---|---|---|
| B-9; | Diuron | 3-(3,4-dichlorophenyl)-1,1-dimethylurea |
| B-10; | Linuron | 3-(3,4-dichlorophenyl)-1-methoxy-1-methylurea |
| B-11; | Isoproturon | 3-(4-isopropylphenyl)-1,1-dimethylurea |
| B-12; | Chlorotoluron | 3-(3-chloro-p-tolyl)-1,1-dimethylurea |
| B-13; | Metobenzuron | N-methoxy-N-methyl-N'-[4-(3,4-dihydro-2-methoxy-2,4,4-trimethyl-2H-1-benzopyran 7-yl-oxy)phenyl]urea |
| B-14; | Tebuthiuron | 1-(5-tert-butyl-1,3,4-thiadiazol-2-yl)-1,3-dimethylurea |
| B-15; | Fluometuron | 1,1-dimethyl-3-( , , -trifluror-m-tolyl)urea |

Triazines

| | | |
|---|---|---|
| B-16; | Simazine | 6-chloro-$N^2,N^4$-diethyl-1,3,5-triazine-2,4-diamine |
| B-17; | Atrazine | 6-chloro-$N^2$-ethyl-$N^4$-isopropyl-1,3,5-triazine-2,4-diamine |
| B-18; | Cyanazine | 2-(4-chloro-6-ethylamino-1,3,5-triazin-2-ylamino)-2-methylpropionitrile |
| B-19; | Terbuthylazine | $N^2$-tert-butyl-6-chloro-$N^4$-ethyl-1,3,5-triazine-2,4-diamine |
| B-20; | Atraton | $N^2$-ethyl-$N^4$-isopropyl-6-methoxy-1,3,5-triazine-2,4-diamine |
| B-21; | Hexazinone | 3-cyclohexyl-6-dimethylamino-1-methyl-1,3,5-triazine-2,4(1H,3H)-dione |

TABLE 2-continued

Herbicides useful for combinations with compounds of table 1. (Note: When a common name has not been assigned a compound, only the chemical name is provided)

| | |
|---|---|
| B-22; Metribuzin | 4-amino-6-tert-butyl-3-methylthio-1,2,4-triazin-5(4H)-one |
| B-23; Simetryn | $N^2,N^4$-diethyl-6-methylthio-1,3,5-triazine-2,4-diamine |
| B-24; Ametryn | $N^2$-ethyl-$N^4$-isopropyl-6-methylthio-1,3,5-triazine-2,4-diamine |
| B-25; Prometryn | $N^2,N^4$-di-isopropyl-6-methylthio-1,3,5-triazine-2,4-diamine |
| B-26; Dimethametryn | $N^2$-(1,2-dimethylpropyl)-$N^4$-ethyl-6-methylthio-1,3,5-triazine-2,4-diamine |
| B-27; Triaziflam | (RS)-N-[2-(3,5-dimethylphenoxy)-1-methylethyl]-6-(1-fluoro-1-methylethyl)-1,3,5-triazine-2,4-diamine |
| Anilides | |
| B-28; Propanil | 3',4'-dichloropropionanilide |
| B-29; Cypromid | 3',4'-dichlorocyclopropanecarboxanilide |
| Hydroxybenzonitriles | |
| B-30; Bromoxynil | 3,5-dibromo-4-hydroxybenzonitrile |
| B-31; Ioxynil | 4-hydroxy-3,5-di-iodobenzonitrile |
| Quaternary ammonium salts | |
| B-32; Paraquat | 1,1'-dimethyl-4,4'-bipyridinium |
| B-33; Paraquat dibromide | 1,1'-dimethyl-4,4'-bipyridinium dibromide salt |
| B-34; Diquat | 1,1'-ethylene-2,2'-bipyridyldiylium |
| B-35; Difenzoquat | 1,2-dimethyl-3,5-diphenylpyrazolium |
| Diphenyl ethers | |
| B-36; Lactofen | ethyl O-[5-(2-chloro-, ,-trifluoro-p-tolyloxy)-2-nitrobenzoyl]-DL-lactate |
| B-37; Acifluorfen | 5-(2-chloro-, ,-trifluoro-p-tolyloxy)-2-nitrobenzoic acid |
| B-38; Acifluorfen sodium | 5-(2-chloro-, ,-trifluoro-p-tolyloxy)-2-nitrobenzoic acid, monosodium salt |
| B-39; Oxyfluorfen | 2-chloro-, ,-trifluoro-p-tolyl 3-ethoxy-4-nitrophenyl ether |
| B-40; Fomesafen | 5-(2-chloro-, ,-trifluoro-p-tolyloxy)-N-methylsulfonyl-2-nitrobenzamide |
| B-41; Bifenox | methyl 5-(2,4-dichlorophenoxy)-2-nitrobenzoate |
| B-42; Chlomethoxyfen | 5-(2,4-dichlorophenoxy)-2-nitroanisole |
| Triketones | |
| B-43; Sulcotrione | 2-(2-chloro-4-methylsulphonylbenzoyl)-1,3-cyclohexanedione |
| B-44; Mesotrione | 2-(4-methylsulphonyl-2-nitrobenzoyl)-1,3-cyclohexanedione |
| Aryloxyphenoxypropionic acids | |
| B-45; Diclofop-methyl | (RS)-2-[4-(2,4-dichlorophenoxy)phenoxy]propionic acid, methyl ester |
| B-46; Pyrofenop-sodium | |
| B-47; Fluazifop-butyl | (RS)-2-[4-(5-trifluoromethyl-2-pyridyloxy)phenoxy]propionic acid, butyl ester |
| B-48; Fluazifop-p-butyl | (R)-2-[4-(5-trifluoromethyl-2-pyridyloxy)phenoxy]propionic acid, butyl ester |
| B-49; Haloxyfop-methyl | (RS)-2-[4-(3-chloro-5-trifluoromethyl-2-pyridyloxy)phenoxy]propionic acid |
| B-50; Quizalofop-p-ethyl | (R)-2-[4-(6-chloroquinoxalin-2-yloxy)phenoxy]propionic acid, ethyl ester |
| B-51; Quizalofop-p-tefuryl | (R)-2-[4-(6-chloroquinoxalin-2-yloxy)phenoxy]propionic acid tetrahydrofurfuryl ester |
| B-52; Fenoxaprop-ethyl | (RS)-2-[4-(6-chloro-1,3-benzoxazol-2-yloxy)phenoxy]propionic acid, ethyl ester |
| B-53; Fenoxaprop-p-ethyl | (R)-2-[4-(6-chloro-1,3-benzoxazol-2-yloxy)phenoxy]propionic acid, ethyl ester |
| B-54; Cyhalofop-butyl | (R)-2-[4-(4-cyano-2-fluorophenoxy)phenoxy]propionic acid, butyl ester |
| B-55; Clodinafop-p-propargyl | (R)-2-[4-(5-chloro-3-fluoro-2-pyridyloxy)phenoxy]-propionic acid, propargyl ester |
| Oximes | |
| B-56; Alloxydim-sodium | methyl (E)-(RS)-3-[1-(allyloxyimino)butyl]-4-hydroxy-6,6-dimethyl-2-oxocyclohex-3-enecarboxylate, sodium salt |
| B-57; Sethoxydim | (RS)-(EZ)-2-(1-ethoxyiminobutyl)-5-[2-(ethylthio)propyl]-3-hydroxycyclohex-2-enone |

TABLE 2-continued

Herbicides useful for combinations with compounds of table 1. (Note: When a common name has not been assigned a compound, only the chemical name is provided)

| | | |
|---|---|---|
| B-58; Clethodim | (RS)-2-[(E)-1-[(E)-3-chloroallyloxyimino]propyl]-5-[2-(ethylthio)propyl]-3-hydroxycyclohex-2-enone | |
| B-59; Tepraloxydim | (EZ)-(RS)-2-{1-[(2E)-3-chloroallyloxyimino]propyl}-3-hydroxy 5-perhydropyran-4-ylcyclohex-2-en-1-one | |
| B-60; Tralkoxydim | 2-[1-(ethoxyimino)propyl]-3-hydroxy-5-mesitylcyclohex-2-enone | |
| B-61; Cycloxydim | (RS)-2-[1-(ethoxyimino)butyl]-3-hydroxy-5-thian-3-ylcyclohex-2-enone | |

Sulfonylureas

| | |
|---|---|
| B-62 ;Chlorimuron-methyl | 2-(4-chloro-6-methoxypyrimidin-2-ylcarbamoylsulfamoyl)benzoic acid, methyl ester |
| B-63; Nicosulfuron | 2-(4,6-dimethoxypyrimidin-2-ylcarbamoylsulfamoyl)-N,N-dimethylnicotinamide |
| B-64; Metsulfuron-methyl | 2-(4-methoxy-6-methyl-1,3,5-triazin-2-ylcarbamoylsulfamoyl)benzoic acid |
| B-65; Triasulfuron | 1-[2-(2-chloroethoxy)phenylsulfonyl]-3-(4-methoxy-6-methyl-1,3,5-triazin-2-yl)urea |
| B-66; Primisulfuron-methyl | 3-[4,6-bis(difluoromethoxy)pyrimidin-2-yl]-1-(2-methoxycarbonylphenylsulphonyl)urea, |
| B-67; Tribenuron-methyl | 2-[4-methoxy-6-methyl-1,3,5-triazin-2-yl(methyl)carbamoylsulfamoyl]benzoic acid, methyl ester |
| B-68; Chlorosulfuron | 1-(2-chlorophenylsulfonyl)-3-(4-methoxy-6-methyl-1,3,5-triazin-2-yl)urea |
| B-69; Bensulfuron-methyl | 2-[[[[[(4,6-dimethoxy-2-pyrimidinyl)amino]carbonyl] amino]sulfonyl]methyl]benzoic acid, methyl ester |
| B-70; Sulfometuron-methyl | 2-(4,6-dimethylpyrimidin-2-ylcarbamoylsulfamoyl) benzoic acid, methyl ester |
| B-71; Prosulfuron | N-[[(4-methoxy-6-methyl-1,3,5-triazin-2-yl)amino]carbonyl]-2-(3,3,3-trifluuoropropyl)benzenesulfonamide |
| B-72; Halosulfuron | 3-chloro-5-(4,6-dimethoxypyrimidin-2-ylcarbamoylsulfamoyl)-1-methylpyrazole-4-carboxylic acid |
| B-73; Halosulfuron-methyl | 3-chloro-5-(4,6-dimethoxypyrimidin-2-ylcarbamoylsulfamoyl)-1-methylpyrazole-4-carboxylic acid, methyl ester |
| B-74; Thifensulfuron-methyl | 3-(4-methoxy-6-methyl-1,3,5-triazin-2-ylcarbamoyl sulfamoyl)thiophen-2-carboxylic acid methyl ester |
| B-75; Rimsulfuron | N-[[(4,6-dimethoxy-2-pyrimidinyl)amino]carbonyl]-3-(ethylsulfonyl)-2-pyridinesulfonamide |
| B-76; Azimsulfuron | 1-(4,6-dimethoxypyrimidin-2-yl)-3-[1-methyl-4-(2-methyl-2H-tetrazol-5-yl)pyrazol-5-ylsulfonyl]urea |
| B-77; Flazasulfuron | 1-(4,6-dimethoxypyrimidin-2-yl)-3-(3-trifluoromethyl-2-pyridylsulfonyl)urea |
| B-78; Imazosulfuron | 1-(2-chloroimidazo[1,2-a]pyridin-3-ylsulfonyl)-3-(4,6-dimethoxypyrimidin-2-yl)urea |
| B-79; Cyclosulfamuron | 1-[2-(cyclopropylcarbonyl)anilinosulfonyl]-3-4,6-dimethoxypyrimidin-2-yl)urea |
| B-80; Flupyrsulfuron | 2-(4,6-dimethoxypyrimidin-2-ylcarbamoylsulfamoyl)-6-trifluoromethylnicotinic acid |
| B-81; Iodosulfuron | 4-iodo-2-[3-(4-methoxy-6-methyl-1,3,5-triazin-2-yl)ureidosulfonyl]benzoic acid |
| B-82; Ethoxysulfuron | 1-(4,6-dimethoxypynrimidin-2-yl)-3-(2-ethoxyphenoxysulfonyl)urea |
| B-83; Flucarbazone | N-(2-trifluoromethoxyphenylsulfonyl)-4,5-dihydro-3-methoxy-4-methyl-5-oxo-1H-1,2,4-triazole-1-carboxamide |
| B-84; Sulfosulfuron | 1-(4,6-dimethoxypyrimidin-2-yl)-3-(2-ethylsulfonyl imidazo [1,2-a]pyridin-3-ylsulfonyl)urea |
| B-85; Oxasulfuron | oxetan-3-yl 2-[(4,6-dimethylpyrimidin-2-yl) carbamoyl sulfamoyl]benzoate |
| B-86; Foramsulfuron | 1-(4,6-dimethoxypyrimidin-2-yl)-3-(2-dimethyl carbamoyl-5-formamidophenylsulfonyl)urea |

Imidazolinones

| | |
|---|---|
| B-87; Imazapyr | 2-(4-isopropyl-4-methyl-5-oxo-2-imidazolin-2-yl)nicotinic acid |
| B-88; Imazethapyr | (RS)-5-ethyl-2-(4-isopropyl-4-methyl-5-oxo-2-imidazolin-2-yl)nicotinic acid |
| B-89; Imazaquin | (RS)-2-(4-isopropyl-4-methyl-5-oxo-2-imidazolin-2-yl)-5-yl)quinoline-3-carboxylic acid |
| B-90; Imazamox | 2-(4-isopropyl-4-methyl-5-oxo-2-imidazolin-2-yl)-5-methoxymethylnicotinic acid |
| B-91; Imazamethabenz | reaction mixture of (RS)-6-(4-isopropyl-4-methyl-5-oxo-2-imidazolin-2-yl)-m-toluic acid and (RS)-2-(4-isopropyl-4-methyl-5-oxo-2-imidazolin-2-yl)-p-toluic |

TABLE 2-continued

Herbicides useful for combinations with compounds of table 1. (Note: When a common name has not been assigned a compound, only the chemical name is provided)

| | |
|---|---|
| B-92; Imazapic | acid, methyl esters<br>(RS)-2-(4,5-dihydro-4-isopropy1-4-methyl-5-oxoimidazol-2-yl)-5-methylnicotinic acid |

Dinitroanilines

| | |
|---|---|
| B-93; Trifluralin | , , -trifluoro-2,6-dinitro-N,N-dipropyl-p-toluidine |
| B-94; Oryzalin | 3,5-dinitro-$N^4$,$N^4$-dipropylsulfanilamide |
| B-95; Pendimethalin | N-(1-ethylpropyl)-2,6-dinitrro-3,4-xylidine |
| B-96; Ethalfluralin | N-ethyl- , , -trifluoro-N-(2-methylally)-2,6-dinitro-p-toluidine |
| B-97; Benfluralin | N-butyl-N-ethyl- , , -trifluoro-2,6-dinitro-p-toluidine |
| B-98; Prodiamine | 2,6-dinitro-$N^1$,$N^1$-dipropyl-4-trifluoromethyl-m-phenylenediamine |

Chloroacetanilides

| | |
|---|---|
| B-99; Alachlor | 2-chloro-2',6'-diethyl-N-methoxymethyl-acetanilide |
| B-100; Metolachor | 2-chloro-6'-ethyl-N-(2-methoxy-1-methylethyl)aceto-o-toluidide |
| B-101; Metolachor-S | (S)-2-chloro-N-(2-ethyl-6-methylphenyl)-N-(2-methoxy-1-methylethyl)acetamide |
| B-102; Propachlor | 2-chloro-N-isopropylacetanilide |
| B-103; Acetochlor | 2-chloro-N-ethoxymethyl-6'-ethylacet-o-toluidide |
| B-104 Acetochlor-S | |
| B-105; Propisochlor | 2-chloro-6'-ethyl-N-isopropoxymethylaceto-o-toluidide |
| B-106; Dimethenamid | 2-chloro-N-[(1-methy-2-methoxyl)ethyl]-N-(2,4-dimethyl-3-thienyl)-acetamide |

Oxyacetamides

| | |
|---|---|
| B-107; Flufenacet | N-(4-fluorophenyl)-N-(1-methylethyl)-2-[[5-[(trifluoromethyl)-1,3,4-thiadiazol-2-yl]oxy]acetamide |

Thiocarbamates

| | |
|---|---|
| B-108; Thiobencarb | S-4-chlorobenzyl diethyl(thiocarbamate) |
| B-109; EPTC, | S-ethyl dipropylthiocarbamate |
| B-110; Triallate | S-2,3,3-trichloroallyl di-isopropylthiocarbamate |
| B-111; Molinate | S-ethyl azepane-1-carbothioate |
| B-112; Pebulate | S-propyl butyl(ethyl)thiocarbamate |
| B-113; Cycloate | S-ethyl cyclohexyl(ethyl)thiocarbamate |
| B-114; Butylate | S-ethyl di-isobutylthiocarbamate |
| B-115; Vemolate | S-propyl dipropylthiocarbamate |
| B-116; Prosulfocarb | S-benzyl dipropylthiocarbamate |

Amides

| | |
|---|---|
| B-117; Diphenamid | N,N-dimethyldiphenylacetamide |

Semicarbazones

| | |
|---|---|
| B-118; Diflufenzopyr | 2-{1-[4-(3,5-difluorophenyl)semicarbazono]ethyl}-nicotinic acid |

Triazolinones

| | |
|---|---|
| B-119;Carfentrazone-ethyl | (RS)-2-chloro-3-[2-chloro-5-(4-difluoromethyl)-4,5-dihydro-3-methyl-5-oxo-1H-1,2,4-triazol-1-yl)-4-fluorophenyl]propionic acid, ethyl ester |
| B-120; Sulfentrazone | N-(2,4-dichloro-5-(4-(difluoromethyl)-4,5-dihydro-3-methyl-5-oxo-1$\underline{H}$-1,2,4-triazol-1-yl)phenyl)methanesulfonamide |
| B-121; Amicarbazone | 4-amino-N-(1,1-dimethylethyl)-4,5-dhihydro-3-(1-methylethyl)-5-oxo-1H-1,2,4-triazole-1-carboxamide |

N phenylphthalimides

| | |
|---|---|
| B-121; Flumioxazin | 2-(7-fluoro-3,4-dihydro-3-oxo-4-(2-propynyl)-2H-1,4-benzoxazin-6-yl)-4,5,6,7-tetrahydro-1H-isoindole-1,3(2H)-dione |

Substituted uracils

| | |
|---|---|
| B-123; Benzfendizone | methyl 2-{5-ethyl-2-[4-(1,2,3,6-tetrahydro-3-methyl-2,6-dioxo-4-trifluoromethylpyrimidin-1-yl)phenoxymethyl]phenoxy}propionate |
| B-124; Butafenacil | 2-chloro-5-[3,6-dihydro-3-methyl-2,6-dioxo-4-(trifluoromethyl)-1(2H)-pyrimidinyl]benzoic acid 1,1-dimethyl-2-oxo-2-(2-propenyloxy)ethyl ester |
| B-125; | 1-Amino-3-(4-chloro-2-fluoro-5-phenoxyphenyl)-6-(trifluoromethyl)-2,4(1H,3H)-pyrimidinedione |
| B-126; | N-[3-Chloro-6-(3,6-dihydro-3-methyl-2,6-dioxo-4- |

TABLE 2-continued

Herbicides useful for combinations with compounds of table 1. (Note: When a common name has not been assigned a compound, only the chemical name is provided)

| | | |
|---|---|---|
| B-127; | | (trifluoromethyl)-1(2H)-pyrimidinyl)-5-fluoro-2-methoxyphenyl]-2-naphthalenecarboxamide<br>[3-Chloro-6-(3,6-dihydro-3-methyl-2,6-dioxo-4-(trifluoromethyl)-1(2H)-pyrimidinyl)-5-fluoro-2-methoxyphenyl]-carbamic acid, (3-nitrophenyl)methyl ester |
| B-128; | | 1-Amino-3-[4-chloro-2-fluoro-5-(2-nitrophenoxy) phenyl]-6-(trifluoromethyl)-2,4(1H,3H)-pyrimidinedione |
| | | Isoxazolidinones |
| B-129; | Clomazone | 2-(2-chlorophenyl)methyl-4, 4-dimethyl-3-isoxazolidinone |
| | | Quinoline carboxylic acids |
| B-130; | Quinclorac | 3,7-dichloro-8-quinolinecarboxylic acid |
| | | Isoxazoles |
| B-131; | Isozaflutole | 5-cyclopropyl-4-(2-methylsulphonyl-4-trifluoromethyl-benzoyl isoxazole |
| | | Triazolopyridinones |
| B-132; | Azafenidin | 2-(2,4-dichloro-5-prop-2-ynyloxyphenyl)-5,6,7,8-tetrahydro-1,2,4-triazolo[4,3-a]pyridin-3(2H)-one |
| | | Amino acids |
| B-133; | Glyphosate | Phosphonomethyl-glycine |
| B-134; | Glufosinate | (RS)-2-amino-4-(hydroxymethylphosphonyl)butanoic acid |

The blend ratio of one substituted acetanilide derivative and one other specific herbicidal compound can not generally be defined, since it varies depending on the time and method of application, weather conditions, soil type and type of formulation. However one other specific herbicidal compound may be incorporated usually in an amount of 0.001 to 1000 parts by weight, preferably 0.005 to 500 parts by weight, per one part by weight of one substituted acetanilide derivative. Further, the total dose of all of the active ingredients is usually from 1 to 10000 g/ha, preferably from 5 to 2000 g/ha. The present invention covers such herbicidal compositions.

The compositions of the present invention exhibit additive or synergistic effects. The compositions can be used for a wide range of applications, for example on crop lands such as paddy fields, upland maize, soybean, wheat and cotton farms, orchards and mulberry fields, and non-crop lands such as forests, farm roads, playgrounds, and factory sites. The application method may be suitably selected for soil treatment application and foliar application.

The active ingredients are formulated with inert ingredients known to the art to facilitate either the suspension, dissolution or emulsification of the active ingredients for the desired use. The type of formulation prepared recognizes the facts that formulation, crop and use pattern all can influence the activity and utility of the active ingredients in a particular use. Thus for agricultural use the present compositions may be formulated as water dispersible granules, granules for direct application to soils, water soluble concentrates, wettable powders, dusts, solutions, emulsifiable concentrates (EC), microemulsion, suspoemulsion, invert emulsion or other types of formulations, depending on the desired weed targets, crops and application methods.

These herbicidal formulations may be applied to the target area (where suppression of unwanted vegetation is the objective) as dusts, granules or water or solvent diluted sprays. These formulation may contain as little as 0.1% to as much as 97% active ingredients by weight.

Dusts are admixtures of the active ingredients with finely ground materials such as clays (some examples include kaolin and montmorillonite clays), talc, granite dust or other organic or inorganic solids which act as dispersants and carriers for the active ingredient; these finely ground materials have an average particle size of less than 50 microns. A typical dust formulation will contain 1% active ingredient and 99% carrier.

Wettable powders are composed of finely ground particles which disperse rapidly in water or other spray carriers. Typical carriers include kaolin clays, Fullers earth, silicas and other absorbent, wettable inorganic materials. Wettable powders can be prepared to contain from 1 to 90% active ingredient, depending on the desired use pattern and the absorbability of the carrier. Wettable powders typically contain wetting or dispersing agents to assist dispersion in water or other carriers.

Water dispersible granules are granulated solids that freely disperse when mixed in water. This formulation typically consists of the active ingredients (0.1% to 95% active ingredient), a wetting agent (1–15% by weight), a dispersing agent (1 to 15% by weight) and an inert carrier (1–95% by weight). Water dispersible granules can be formed by mixing the ingredients intimately then adding a small amount of water on a rotating disc (said mechanism is commercially available) and collecting the agglomerated granules. Alternatively, the mixture of ingredients may be mixed with an optimal amount of liquid (water or other liquid) and passed through an extruder (said mechanism is commercially available) equipped with passages which allow for the formation of small extruded granules. Alternatively, the mixture of ingredients can be granulated using a high speed mixer (said mechanism is commercially available) by adding a small amount of liquid and mixing at high speeds to affect agglomeration. Alternatively, the mixture of ingredients can be dispersed in water and dried by spraying the dispersion through a heated nozzle in a process known as spray drying (spray drying equipment is commercially available). After granulation the moisture content of granules is adjusted to an optimal level (generally less than 5%) and the product is sized to the desired mesh size.

Granules are granulated solids that do not disperse readily in water, but instead maintain their physical structure when applied to the soil using a dry granule applicator. These granulated solids may be made of clay, vegetable material such as corn cob grits, agglomerated silicas or other agglomerated organic or inorganic materials or compounds such as calcium sulfate. The formulation typically consists of the active ingredient (1 to 20%) dispersed on or absorbed into the granule. The granule may be produced by intimately mixing the active ingredients with the granules with or without a sticking agent to facilitate adhesion of the active ingredients to the granule surface, or by dissolving the active ingredients in a solvent, spraying the dissolved active ingredients and solvent onto the granule then drying to remove the solvent. Granular formulations are useful where in-furrow or banded application is desired.

Emulsifiable concentrates (EC) are homogeneous liquids composed of a solvent or mixture of solvents such as xylenes, heavy aromatic naphthas, isophorone or other proprietary commercial compositions derived from petroleum distillates, the active ingredient and an emulsifying agent or agents. The EC is added to water (or other spray carrier) and applied as a spray to the target area. The composition of an EC formulation can contain 0.1% to 95% active ingredient, 5 to 95% solvent or solvent mixture and 1 to 20% emulsifying agent or mixture of emulsifying agents.

Suspension concentrate (also known as flowable) formulations are liquid formulations consisting of a finely ground suspension of the active ingredient in a carrier, typically water or a non-aqueous carrier such as an oil. Suspension concentrates typically contain the active ingredients (5 to 50% by weight), carrier, wetting agent, dispersing agent, anti-freeze, viscosity modifiers and pH modifiers. For application, suspension concentrates are typically diluted with water and sprayed on the target area.

Solution concentrates are solutions of the active ingredient (1 to 70%) in solvents which have sufficient solvency to dissolve the desired amount of active ingredients. Because they are simple solutions without other inert ingredients such as wetting agents, additional additives are usually added to the spray tank mix before spraying to facilitate proper application.

Microemulsions are solutions consisting of the active ingredients (1 to 30%) dissolved in a surfactant or emulsifier, without any additional solvents. There are no additional solvents added to this formulation. Microemulsions are particularly useful when a low odor formulation is required such as in residential turfgrass applications.

Suspoemulsions are combinations of two active ingredients. One active ingredient is made as a suspension concentrate (1–50% active ingredient) and the second active ingredient is made as a emulsifiable concentrate (0.1 to 20%). A reason for making this kind of formulation is the inability to make an EC formulation of the first ingredient due to poor solubility in organic solvents. The suspoemulsion formulation allows for the combination of the two active ingredients to be packaged in one container, thereby minimizing packaging waste and giving greater convenience to the product user.

The compositions of the present invention may be used in admixture with or in combination with other agricultural chemicals, fertilizers, adjuvants, surfactants, emulsifiers, oils, polymers or phytotoxicity-reducing agents such as herbicide safeners. In such a case, they may exhibit even better effects or activities. As other agricultural chemicals, herbicides, fungicides, antibiotics, plant hormones, plant growth regulators, insecticides, acaricides or nematicides may, for example, be mentioned. Certain tank mix additives such as spreader stickers, penetration aids, wetting agents, surfactants, emulsifiers, humectants and UV protectants may be added in amounts of 0.01% to 5% to enhance the biological activity, stability, wetting, spreading on foliage or uptake of the active ingredients on the target area of to improve the suspensibility, dispersion, redispersion, emulsifiability, UV stability or other physical or physico-chemical property of the active ingredients in the spray system or target area.

A few formulation examples of the present invention are given as follows.

FORMULATION EXAMPLE 1

Emulsifiable Concentrate

| | |
|---|---|
| Each of compound A-1 to A-23 | 0.1–95% wt./wt. |
| Each of compound B-1 to B-134 | 0.1–95% wt./wt. |
| Calcium sulfonate and nonionic surfactant blend | 4–12% wt./wt. |
| Aromatic hydrocarbon | QS to 100% |

FORMULATION EXAMPLE 2

Suspension Concentrate

| | |
|---|---|
| Each of compound A-1 to A-23 | 1–70% wt./wt. |
| Each of compound B-1 to B-134 | 1–70% wt./wt. |
| Proylene gylcol | 3–6% wt./wt. |
| Silicone defoamer | 0.2–1% wt./wt. |
| Xanthan gum | 0.1–0.3% wt./wt. |
| Napthalene formaldehyde condensate | 2–6% wt./wt. |
| Octylphenol ethoxylate | 1–4% wt./wt. |
| 1,2 benziso-thiazolin-3-one | 0.05–0.25% wt./wt. |
| Water | QS to 100% |

FORMULATION EXAMPLE 3

Wettable Powder

| | |
|---|---|
| Each of compound A-1 to A-23 | 1–90% wt./wt. |
| Each of compound B-1 to B-134 | 1–90% wt./wt. |
| Sodium-N-methyl-N-oleoyl taurate | 1–4% wt./wt. |
| Napthalene Sulfonate | 4–10% wt./wt. |
| Kaolin clay | QS to 100% |

FORMULATION EXAMPLE 4

Water Dispersible Granule

| | |
|---|---|
| Each of compound A-1 to A-23 | 0.1–95% wt./wt. |
| Each of compound B-1 to B-134 | 0.1–95% wt./wt. |
| Napthalene formaldehyde condensate | 3–10% wt./wt. |
| Sodium alkyl napthalene sulfenate | 1–4% wt/wt. |
| Kaolin Clay | QS to 100% |

TEST EXAMPLE 1

Seeds of weed species were sown in 10 cm square plastic pots containing a 3:2:1 sand:soil:peat mixture. Species included six broadleaf weeds, CASOB (Cassia obtusifolia, L., sicklepod), IPOHE (*Ipomoea hederacea*, L., ivyleaf morningglory), ABUTH (*Abutilon theophrastii*, velvetleaf, AMARE (*Amaranthus retroflexus*, redroot pigweed), CHEAL (*Chenopodium album*, lambsquarters) and XANST (*Xanthium strumarium*, cocklebur ), four grass weeds, SORHA (*Sorghum halepense*, johnsongrass), SETVI (*Setaria viridis*, green foxtail), ECHCG (*Echinochloa crusgalli*, bamyardgrass), and DIGSA (*Digitria sanguinalis*, large crabgrass) and four crops species, *Zea mays*, *Glycine max* L. *Triticum aestivum*, and *Oryza sativa*. Herbicide treatments were applied in water carrier via automated track sprayer to the soil surface of these pots 1 day after planting. The sprayer was calibrated to deliver the material in a volume of 187 l/ha through a TJ8001E spray nozzle at a pressure of 40 PSI.

Treatments included the compounds of formula I numbers 1, 15, 16 and 23, the commercial grass herbicides metolachlor S (Dual II Magnum®), acetochlor (Harness®), alachlor (Lasso MT®) alone and in combination with three broadleaf herbicides, atrazine, isoxaflutole and compound B-128 (Table 2). All grass herbicides (compounds 1, 15, 16, 23, metolachlor S, acetochlor and alachor were applied at a rate of 1000 g/ha. The broadleaf herbicides were applied at 1680 g/ha for atrazine, 78 g/ha for isoxaflutole and 125 g/ha for B-128.

After treatment, pots were returned to a greenhouse where they were watered and held in good growth conditions for two weeks. At the end of two weeks, herbicidal efficacy was evaluated visually using a rating system from 0–100%, where 0=no inhibition of growth, and 100=complete death of all plants in the testing unit. Results are reported in table 3 as the mean control of all six broadleaf weeds, mean control of all four grass weeds and the phytotoxicity to maize.

TABLE 3

Weed control of combinations of acetanilides and broadleaf herbicides.

| Treatment | broadleaf control | Grass control | Phytotoxicity |
|---|---|---|---|
| Cpd 1 | 22 | 100 | 5 |
| Cpd 23 | 33 | 100 | 33 |
| Cpd 15 | 32 | 100 | 5 |
| Cpd 16 | 53 | 100 | 3 |
| metolachlor | 41 | 100 | 0 |
| acetochlor | 75 | 100 | 8 |
| dimethenamid | 68 | 100 | 30 |
| Cpd 1 + atrazine | 99 | 100 | 11 |

TABLE 3-continued

Weed control of combinations of acetanilides and broadleaf herbicides.

| Treatment | broadleaf control | Grass control | Phytotoxicity |
|---|---|---|---|
| Cpd 23 + atazine | 99 | 100 | 99 |
| Cpd 15 + atrazine | 100 | 100 | 15 |
| Cpd 16 + atrazine | 100 | 100 | 13 |
| Metolachlor + atrazine | 100 | 100 | 3 |
| Acetochlor + atrazine | 100 | 100 | 5 |
| Dimethenamid + atrazine | 100 | 100 | 9 |
| Cpd 1 + isoxaflutole | 91 | 100 | 35 |
| Cpd 23 + isoxaflutole | 89 | 100 | 83 |
| Cpd 15 + isoxaflutole | 87 | 100 | 58 |
| Cpd 16 + isoxaflutole | 92 | 100 | 25 |
| Metolachlor + isoxaflutole | 92 | 100 | 25 |
| Acetochlor + isoxaflutole | 95 | 100 | 33 |
| Dimethenamid + isoxaflutole | 94 | 100 | 45 |
| Cpd 1 + B-128 | 94 | 100 | 3 |
| Cpd 23 + B-128 | 97 | 100 | 30 |
| Cpd 15 + B-128 | 96 | 100 | 15 |
| Cpd 16 + B-128 | 97 | 100 | 10 |
| Metolachlor + B-128 | 97 | 100 | 13 |
| Acetochlor + B-128 | 99 | 100 | 6 |
| Dimethenamid + B-128 | 100 | 100 | 13 |

Compound 23 exhibits an unusual phytotoxicity compared to compounds 1, 15 and 16. Thus, compound 23 is moderately more phytotoxic when used alone compared to compounds 1,15 and 16, but when used in combination with atrazine and isoxaflutole it causes severe phytotoxicity to maize. This result is unexpected within the group of compounds of formula I and shows there is considerable variability within the compounds of formula I for ability to combine with other herbicides in a safe and effective manner.

TEST EXAMPLE 2

Two field trials were established on contrasting soil types. Trial 1 was on a soil with low organic matter and high sand content, and trial 2 was on a clay loam soil with moderate amounts of organic matter. In both cases, the soil was overseeded (followed by light tillage) with seeds of *Amaranthus retroflexus, Abutilon theophrasti, Chenopodium album, Ipomoea hederacea*, and *Setaria viridis* to ensure consistent weed populations. Maize was planted with 30 inches between rows. Immediately after planting the maize, herbicidal treatments were applied using a boom sprayer equipped with Tee Jet 110-015 nozzles applying the spray solution at a rate of 187 l/hectare. Untreated check plots were included as the basis for comparison of herbicidal efficacy.

Treatments included the compound of formula I number 16, the commercial grass herbicides metolachlor S (Dual II Magnum®), acetochlor (Harness®) and dimethenamid (Frontier®) alone and in combination with two broadleaf herbicides, atrazine and B-128. All grass herbicides (compound 16, metolachlor S, acetochlor and dimethenamid) were applied at a rate of 1000 g/ha. The broadleaf herbicides were applied at 1680 g/ha for atrazine and 150 g/ha for B-128.

Observations on percent weed control and phytotoxicity to maize were made at 35 days after treatment for field trial 1 and 21 days after application for field trial 2. All visual estimates were made in comparison to untreated check plots. Results reported are the mean control of broadleaf weeds, and percent control for *Setaria viridis*, the predominant grassy weed in this experiment. The results of field trial 1 are in table 4 and the results of field trial 2 are in table 5.

TABLE 4

Weed control (in field) of combinations of acetanilides and broadleaf herbicides 35 days after applications. Low organic matter, high sand content soil

| Treatment | broadleaf control | S. viridis control | Phytotoxicity |
|---|---|---|---|
| Cpd 16 | 33 | 96 | 0 |
| Metolachlor S | 40 | 100 | 0 |
| acetochlor | 50 | 99 | 0 |
| dimethenamid | 44 | 100 | 0 |
| Cpd 16+ atrazine | 91 | 99 | 2 |
| Metolachlor S + atrazine | 93 | 100 | 2 |
| Acetochlor + atrazine | 95 | 99 | 4 |
| Dimethenamid + atrazine | 93 | 100 | 5 |
| Cpd 16 + B-128 | 98 | 99 | 2 |
| Metolachlor S + B-128 | 97 | 100 | 2 |
| Acetochlor + B-128 | 99 | 100 | 4 |
| Dimethenamid +B-128 | 98 | 100 | 5 |

TABLE 5

Weed control (in field) of combinations of acetanilides and broadleaf herbicides 21 days after applications. Moderate organic matter, high clay content soil

| Treatment | broadleaf control | S. viridis control | Phytotoxicity |
|---|---|---|---|
| Cpd 16 | 24 | 75 | 2 |
| Metolachlor S | 18 | 60 | 1 |
| acetochlor | 36 | 87 | 1 |
| dimethenamid | 26 | 86 | 1 |
| Cpd 16 + atrazine | 86 | 88 | 2 |
| Metolachlor S + atrazine | 81 | 81 | 2 |
| Acetochlor + atrazine | 87 | 93 | 4 |
| Dimethenamid + atrazine | 74 | 82 | 3 |
| Cpd 16 + B-128 | 86 | 85 | 5 |
| Metolachlor S + B-128 | 80 | 73 | 5 |
| Acetochlor + B-128 | 91 | 96 | 10 |
| Dimethenamid + B-128 | 79 | 83 | 7 |

On sandy, low organic matter soil, compound 16, when combined with atrazine or experimental B-128 performed with equal efficacy as other herbicides. On higher organic, high clay soil, compound 16 performed relatively better than two of the three standards.

What is claimed is:

1. A herbicidal composition comprising as the effective components

A) at least one substituted acetanilide derivative of the formula I:

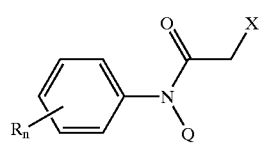

wherein n is an integer of 1 or 2

R is H, halogen, $C_{1-4}$ alkyl or $C_{1-2}$ alkoxy

Q is cyanomethyl or propargyl

X is halogen and

B) at least one compound selected from the group consisting of aryloxyalkanoic acids, aromatic carboxylic acids, ureas, triazines, anilides, hydroxybenzonitriles, quaternary ammonium salts, diphenyl ethers, triketones, aryloxyphenoxypropionic acids, oximes, sulfonylureas, imidazolinones, dinitroanilines, chloroacetanilides, oxyacetamides, thiocarbamates, amides, semicarbazones, triazolinones, N-phenylphthalimides, substituted uracils, isoxazolidinones, quinoline carboxylic acids, isoxazoles, amino acids and triazolopyridinones.

2. The herbicidal composition according to claim 1, wherein the effective component A) is at least one substituted acetanilide derivative of the formula I;

wherein; n is an integer of 1 or 2

R is H, halogen, C1–4 alkyl or C1–2 alkoxy

Q is cyanomethyl or propargyl

X is chlorine.

3. The herbicidal composition according to claim 1, wherein the effective component A) is at least one substituted benzene derivative of the formula I;

wherein n is an integer of 1 or 2

R is H or C1-4 alkyl

Q is cyanomethyl or propargyl

X is chlorine.

4. The herbicidal composition according to claim 1, wherein the effective component A) is at least one substituted acetanilide derivative of the formula I;

wherein n is an integer of 1 or 2

R is methyl or ethyl

Q is cyanomethyl or propargyl

X is chlorine.

5. The herbicidal composition according to claim 1, wherein the effective component A) is 2-chloro-N-cyanomethyl-2',6'-dimethylacetanilide.

6. The herbicidal composition according to claim 1, wherein the effective components A) is 2-chloro-2',6'-diethyl-N-propargylacetanilide.

7. The herbicidal composition according to claim 6 wherein the at least one compound B) is a substituted uracil.

8. The herbicidal composition according to claim 7 wherein the substituted uracil is 1-amino-3-[4-chloro-2-fluoro-5-(2-nitrophenoxy)phenyl]-6-(trifluoromethyl)-2,4 (1H,3H)-pyrimidinedione.

* * * * *